US010302534B2

(12) United States Patent
Rivat et al.

(10) Patent No.: US 10,302,534 B2
(45) Date of Patent: May 28, 2019

(54) FILTER DEVICE FOR FILTERING COMPLEX FLUID SAMPLES

(71) Applicant: MERCK PATENT GMBH, Darmstadt (DE)

(72) Inventors: Philippe Rivat, Dorlisheim (FR); Sylvain Frey, Reutenbourg (FR)

(73) Assignee: MERCK PATENT GMBH, Darmstadt (DE)

( * ) Notice: Subject to any disclaimer, the term of this patent is extended or adjusted under 35 U.S.C. 154(b) by 9 days.

(21) Appl. No.: 14/916,874

(22) PCT Filed: Aug. 6, 2014

(86) PCT No.: PCT/EP2014/002158
§ 371 (c)(1),
(2) Date: Mar. 4, 2016

(87) PCT Pub. No.: WO2015/032464
PCT Pub. Date: Mar. 12, 2015

(65) Prior Publication Data
US 2016/0216177 A1    Jul. 28, 2016

(30) Foreign Application Priority Data

Sep. 5, 2013 (EP) ..................................... 13290211

(51) Int. Cl.
*G01N 1/40* (2006.01)
*B01L 3/00* (2006.01)

(52) U.S. Cl.
CPC .......... *G01N 1/4077* (2013.01); *B01L 3/5635* (2013.01); *B01L 2200/0631* (2013.01);
(Continued)

(58) Field of Classification Search
CPC ........... B01L 3/5635; B01L 2200/0631; B01L 2300/0681; G01N 2001/4088;
(Continued)

(56) References Cited

U.S. PATENT DOCUMENTS 3,831,759 A * 8/1974 Gelman ............... B01D 29/085
 210/232
4,301,010 A * 11/1981 Eddleman ............. B01D 29/05
 210/406

(Continued)

FOREIGN PATENT DOCUMENTS

CN    101312785 A    11/2008
EP    1031371 A1     8/2000
(Continued)

OTHER PUBLICATIONS

International Search Report for PCT/EP2014/002158 dated Mar. 17, 2015.
(Continued)

*Primary Examiner* — Brian R Gordon
(74) *Attorney, Agent, or Firm* — Millen White Zelano & Branigan, PC

(57) ABSTRACT

A filter device (1) for filtering complex fluid samples including a first filter funnel (2) having an inlet (2a), an outlet (2b) and a first internal space (2c), and a second filter funnel (3) having an inlet (3a), an outlet (3b) and a second internal space (3c). The first and second filter funnels (2,3) are sequentially arranged with a first filter medium (4) located therebetween such that a volume of sample fluid placed in the first internal space (2c) can pass through the first filter medium (4) and be collected in the second internal space (3c). An intermediate connector (12) is provided between the first filter medium (4) and the internal space (3c). The intermediate connector (12) has a port (13) and/or a vent for communicating the internal second space (3c) with an
(Continued)

external gas source/atmosphere and/or a vacuum source via a valve arrangement (14).

20 Claims, 11 Drawing Sheets

(52) U.S. Cl.
CPC ... *B01L 2300/0681* (2013.01); *B01L 2300/12* (2013.01); *B01L 2400/049* (2013.01); *B01L 2400/0487* (2013.01); *G01N 2001/4088* (2013.01)

(58) Field of Classification Search
CPC ...... B01D 29/085; B01D 29/09; B01D 29/58; B01D 63/082; B01D 2201/4038; C12M 33/14
USPC .......................................................... 210/335
See application file for complete search history.

(56) References Cited

U.S. PATENT DOCUMENTS

| | | | | |
|---|---|---|---|---|
| 4,357,240 A | * | 11/1982 | Mehra | B01D 29/05 210/455 |
| 4,468,321 A | * | 8/1984 | St. John | B01D 29/05 210/232 |
| 4,783,318 A | | 11/1988 | Lapakko et al. | |
| 5,529,694 A | * | 6/1996 | Strickler | B01D 11/0219 210/416.1 |
| 5,603,900 A | * | 2/1997 | Clark | B01D 29/012 422/535 |
| 5,849,249 A | * | 12/1998 | Jones, Jr. | B01D 11/0219 210/406 |
| 6,277,648 B1 | * | 8/2001 | Colpan | B01D 39/00 210/489 |
| 6,458,278 B1 | * | 10/2002 | Leoncavallo | B01D 29/05 210/321.75 |
| 6,770,203 B2 | | 8/2004 | Leoncavallo et al. | |
| 7,240,572 B2 | * | 7/2007 | Pitt | B01L 3/502 73/863.21 |
| 7,661,538 B1 | * | 2/2010 | Zuk, Jr. | B01D 29/05 210/416.1 |
| 7,798,333 B2 | | 9/2010 | Zuk, Jr. | |
| 7,824,623 B2 | * | 11/2010 | Clark | B01D 61/18 422/509 |
| 8,158,009 B2 | * | 4/2012 | Kane | B01D 29/05 210/739 |
| 8,231,012 B2 | | 7/2012 | Kane | |
| 9,452,373 B1 | * | 9/2016 | Horng | B01L 3/56 |
| 2003/0010708 A1 | | 1/2003 | Leocavallo et al. | |
| 2003/0080045 A1 | * | 5/2003 | Zuk, Jr. | B01D 29/05 210/416.1 |
| 2007/0144959 A1 | | 6/2007 | Zuk, Jr. | |
| 2010/0119416 A1 | * | 5/2010 | Tajima | B01D 15/22 422/400 |
| 2010/0320134 A1 | | 12/2010 | Zuk, Jr. | |
| 2012/0152865 A1 | * | 6/2012 | Lin | B01D 29/085 210/808 |

FOREIGN PATENT DOCUMENTS

| | | |
|---|---|---|
| JP | S49-78585 U | 7/1974 |
| JP | 2010-537797 A | 12/2010 |

OTHER PUBLICATIONS

English Translation of First Office Action for related Chinese Patent Application No. 2014800490441 dated Feb. 13, 2017.
English Translation summary of First Office Action for related JP Patent Application No. 2016-539428 dated Jun. 26, 2018 (1 page).

* cited by examiner

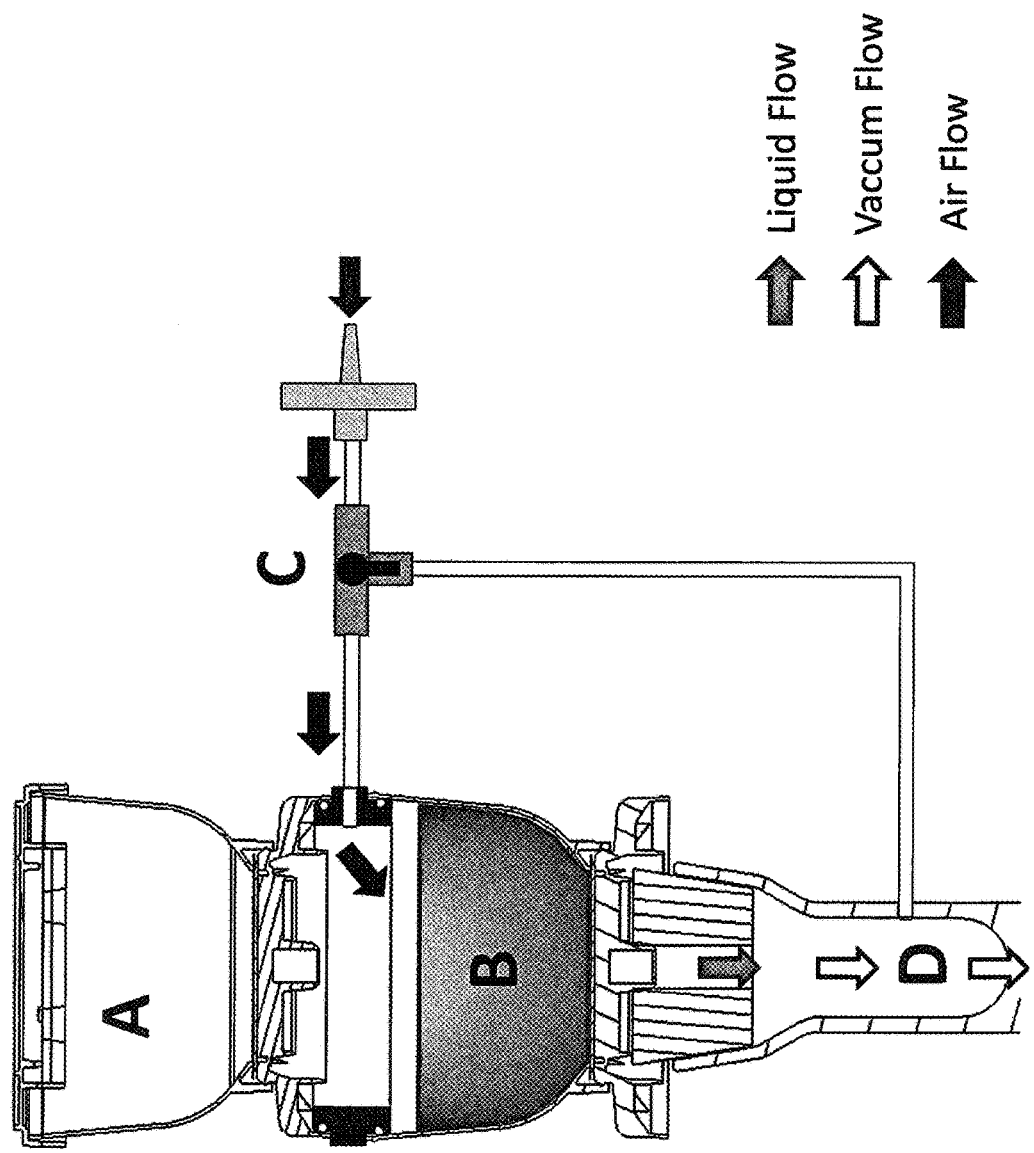

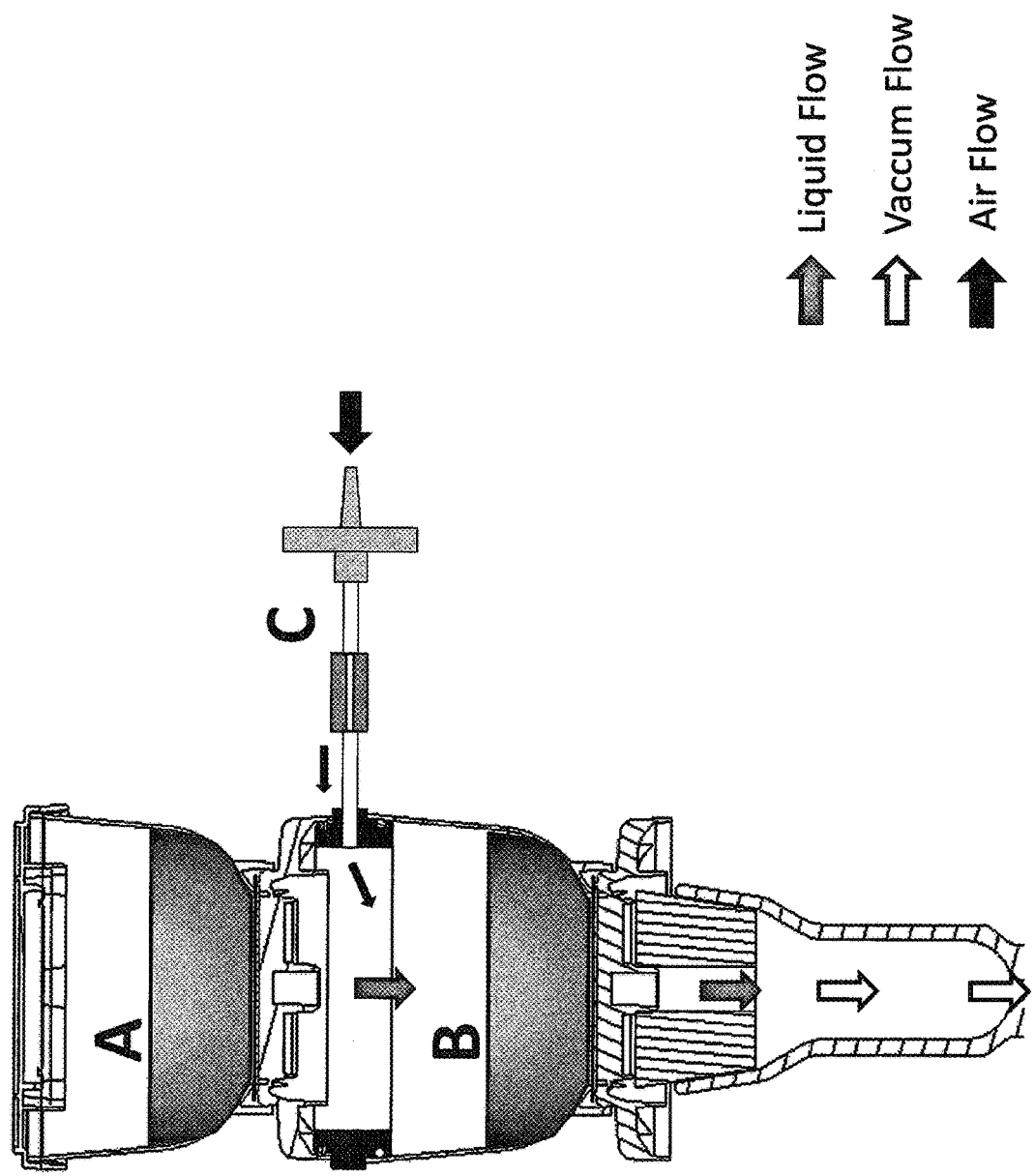

FILTER DEVICE FOR FILTERING COMPLEX FLUID SAMPLES

The present invention concerns a filter device for filtering complex fluid samples. The present invention is particularly applicable in the field of the biopharmaceutical, pharmaceutical, hospital, as well as food and beverage industries for performing bioburden tests with fluid samples that are complex to filter.

Certain fluid samples that are complex to filter require a two-stage filtration process through a first filter or pre-filter including a membrane with large pores which retain large particles from the fluid samples, while the filtrate is collected in a downstream container. The filtrate is subsequently treated by normal filtration in a second stage.

If the two stages are performed in different containers or processes, the handling is complex and the risk of contamination of the retentate and/or the filtrate and/or the fluid samples before testing is high at any point in and between the stages. Furthermore, the capacity of the filter devices for such complex fluid samples is often inappropriate, either too small so that the pores of the filter membrane are plugged very quickly and before the entire volume of the fluid sample has passed the pre-filter, or is too large, leading to excessive cost of the equipment and of cleaning requirements. In the first situation, several devices have to be used until a desired volume of the fluid sample is processed.

In practice there exist several combined pre-filtration/filtration devices in stainless steel. One disadvantage of such combined devices is a very small volume and capacity and difficulties in handling, for example to open and close the respective filter funnels of the device. This leads to a relatively high risk of contamination during the handling and to high cleaning and autoclave requirements of the system in view of the material that is stainless steel. Another disadvantage of such devices is the lack of a possibility to watch the progress of the respective filtration steps so that there is a high risk that the device is opened before the filtration is completed. Simultaneously, in case the filter membrane of the pre-filter stage is plugged, for example, the opening of the filter device risks spilling and/or contamination of the fluid sample remaining still in the container.

It is therefore an object of the present invention to provide a filter device for filtering complex fluid samples in a two-stage process that is ready to use to perform, for example, bioburden tests with such samples that are complex to filter, and in which the above-outlined risks of contamination are minimized and which is easy and safe to handle. Furthermore, the filter device should provide a time-efficient performance of the bioburden testing of the complete fluid sample through at least two stages.

To solve the problem the present invention provides a filter device for filtering complex fluid samples as defined in claim 1. Preferred embodiments of the filter device are defined in the dependent claims.

The filter device of the invention for filtering complex fluid samples has a first filter funnel having an inlet and an outlet and an internal space dimensioned to receive volume of sample fluid to be filtered, and a second filter funnel having an inlet and an outlet and an internal space dimensioned to receive the entire volume of the sample fluid. The first and second filter funnels are sequentially arranged with a first filter medium, preferably a pre-filter, located therebetween such that the volume of sample fluid placed in the internal space of the first filter funnel can pass through the first filter medium and be collected in the internal space of the second filter funnel. According to the invention, an intermediate connector is provided downstream of the first filter medium and upstream of the internal space of the second filter funnel and this intermediate connector has a port and/or a vent for communicating the internal space of the second filter funnel with an external gas source/atmosphere and/or a vacuum source via a valve arrangement.

The filter device of the invention and especially the provision of the intermediate connector with such a port and/or vent and valve arrangement provides the possibility of selectively applying a vacuum or sub-ambient pressure to the internal space of the second filter funnel to promote filtration through the first filter medium from the first filter funnel to the second filter funnel.

Once the entire volume of the sample fluid is collected in the second filter funnel, the port and/or vent and valve arrangement can be used to communicate the internal space of the second filter funnel with the atmosphere to then promote further filtration in the second stage to a downstream receptacle or filter head to which the filter device and especially the second filter funnel can be attached.

By being able to select the level of sub-ambient pressure or vacuum in the second filter funnel by regulating the valve arrangement, by the specification of the leak or of the vent, one can actively control and/or predefine the filtration speed for the purpose of avoiding foam creation and increase the recovery rate. The pressure level set in the second filter funnel can be at a value that is between ambient pressure and the reduced pressure existing in the vacuum filter head downstream of the second filter funnel (or put the other way: the vacuum in the second filter funnel can be smaller than that in the vacuum filter head.

Furthermore, the integration of the first and second filter funnels in the filter device provides an integral unit that can be used as such for subjecting the fluid sample to pre-filtration and main filtration without requiring transport and/or separation of the filter funnels in between the filtration stages. This considerably reduces the risk of contamination in the process and also reduces the time required to carry out the two stages of filtration of such complex fluid samples.

In a preferred embodiment the first and second filter funnels are integrally connected with each other or are releasably connectable with each other. The integral structure further facilitates the handling whereas the releasable connection increases the flexibility and re-use as well as cleaning of the device.

In a preferred embodiment, the first and second filter funnels are connectable through a separate filter holder adapted to support the first filter medium that is preferably the pre-filter in the two-stage process. For this purpose, the first filter funnel is preferably provided with a first connector structure for releasably mechanically and sealingly attaching a mating connector structure of the filter holder to the first filter funnel such that all fluid placed in the internal space of the first filter funnel has to pass the first filter medium in order to be received in the internal space of the second filter funnel.

Furthermore, the filter holder preferably has a second connector structure for releasably mechanically and sealingly attaching to a mating connector structure of the second filter funnel such that all fluid passing the first filter medium is directed to the inlet of the second filter funnel.

The filter holder preferably has a third connector structure different from the second connector structure for releasably mechanically and sealingly attaching to a mating connector structure of a downstream equipment, such that all fluid passing the first filter medium is directed to the downstream equipment, preferably a receptacle or a filter head of processing equipment.

In a preferred embodiment, the intermediate connector is connected or is releasably connectable between the filter holder and the inlet of the second filter funnel. This provides for a modular structure bringing about the possibility to combine various filter holders with the same or different connector structure and the same or different filter funnels. It also facilitates the task of cleaning of the device.

The valve arrangement of the filter device provided in connection with the intermediate connector and its structure preferably comprises a three-way valve and tubing adapted to selectively communicate the internal space of the second filter funnel via the port of the intermediate connector with an external gas source/atmosphere and/or vacuum source.

In an alternative preferred embodiment, the valve arrangement comprises a calibrated leak adapted to communicate with the internal space of the second filter funnel via the port of the intermediate connector with the external gas source/atmosphere.

For both alternatives, the valve arrangement could be either integral with the intermediate connector or externally connected to or connectable to the port of the intermediate connector.

Preferably, the first and/or the second filter funnels is/are at least partially transparent to allow visual inspection of the fluid level in the internal space. This increases the security because the user may monitor the progress of one or both filtration stages, thereby avoiding early opening of the device. Furthermore, any premature clogging of the filter medium in the first and/or second stage can be detected easily.

While the first filter medium is preferably a pre-filter, the second filter funnel can be provided downstream of the outlet with a second filter medium that could be, for example, another pre-filter stage or a main filter.

The entire device can comprise a lid that is releasably attachable to close the inlet of the first filter funnel. The lid can be compatible so as to be also releasably attachable to close the inlet of the second filter funnel. Further lids can be provided to close the outlets of the first and second filter funnels when the device is not in use to avoid contamination.

The first filter funnel (and optionally the second filter funnel, too) can be made disposable and preferably from a plastics material. This option is advantageous if the prefiltration stage involves the retaining of relatively large amounts of particles so that the pre-filter stage carried out by the first filter funnel has to be repeated. In this case, the cost and time are short because the first filter funnel is a disposable part that can be replaced frequently and at low cost.

Preferably, the first and second filter funnels are interchangeable and are preferably identical to reduce the number of parts to be reduced and stocked.

Preferably, the vacuum source is existing in a filter head or other downstream equipment on which the second filter funnel of the filter device can be attached in the process of filtering the complex fluid samples.

BRIEF DESCRIPTION OF FIGURES

A preferred embodiment of the filter device of the present invention will be described as an example by reference to the attached drawing. In the drawing.

Figure 1:
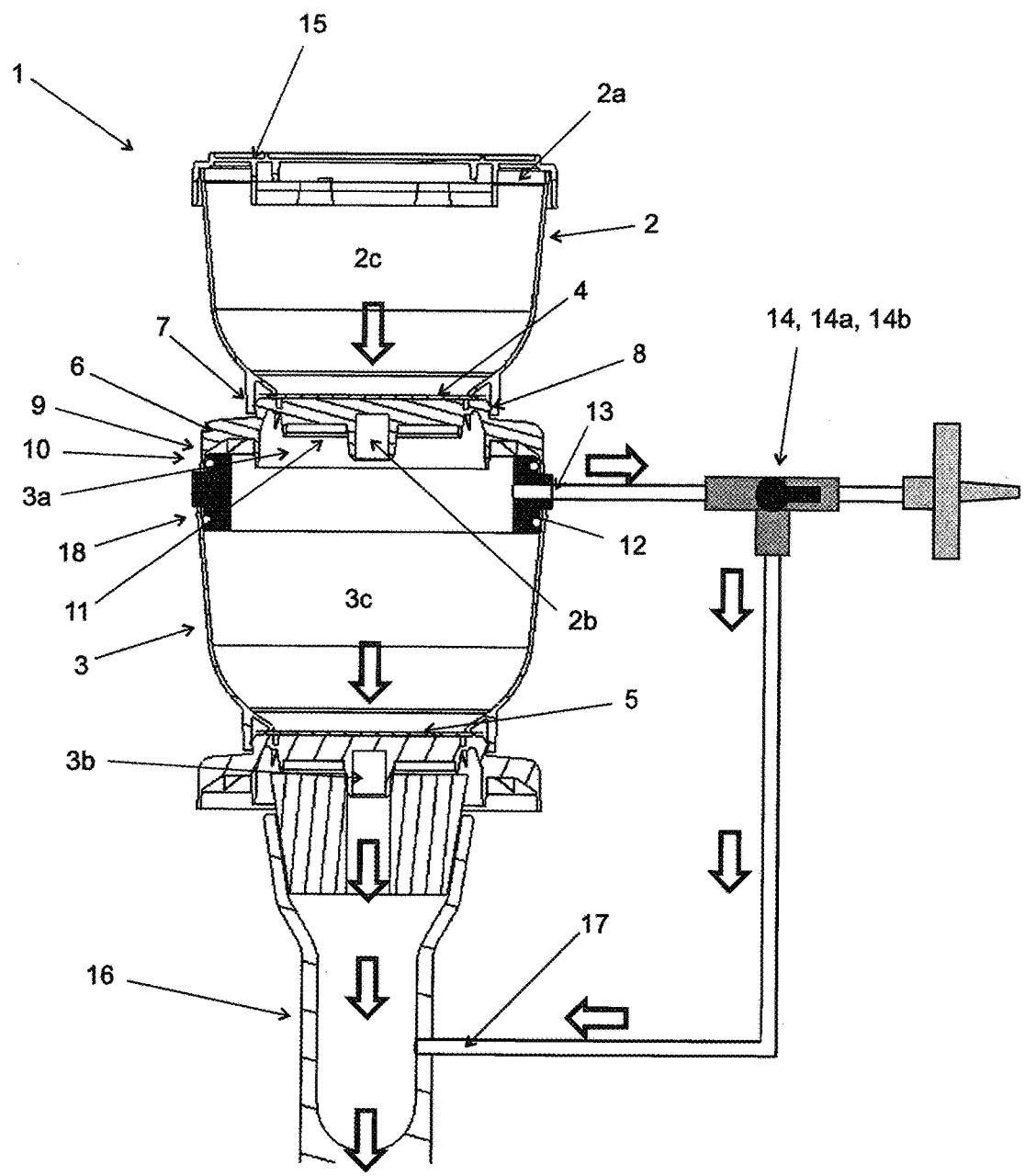
FIG. 1 shows a filter device of the preferred embodiment to explain the various elements.

The filter device 1 of a preferred embodiment for filtering complex fluid samples includes at least two, preferably identical, filter funnels 2, 3, that each have an inlet 2*a*, 3*a*, an outlet 2*b*, 3*b*, and an internal space 2*c*, 3*c* that is dimensioned to receive a desired volume of the sample fluid to be filtered. While the internal space of the first filter funnel can be smaller than that of the second filter funnel, the second filter funnel space should be dimensioned such that it is capable of receiving the entire volume intended to be processed.

The at least two filter funnels are sequentially arranged with a first filter medium 4 located therebetween such that the entire volume of the sample fluid placed in the internal space 2*c* of the first filter funnel 2 can pass through the first filter medium 4 and be collected in the internal space 3*c* of the second filter funnel 3. The first filter medium 4 typically is a pre-filter and can be a single or multiple-layer membrane. It can be fixed or sealed in the filter funnel or can be removably provided therein.

Although the device is described and shown with two filter funnels combined with each other, more than two filter funnels can be sequentially attached, thereby realizing plural filtration stages in sequence. This is particularly simple to realize if the filter funnels are identical and mechanically connectable to each other by mating connecting structures as described further below.

The releasable connection of the filter funnels is preferably effected by means of the filter holder 6 adapted to support the first (or any further) filter medium 4. For this purpose the first filter funnel 2 (or any further filter funnel in case the filter funnels are identical in this respect) is provided with a first connector structure 7 for releasably and mechanically and sealingly attaching a mating connector structure 8 of the filter holder 6 to the first filter funnel 2 such that all fluid placed in the internal space 2*c* of the first filter funnel 2 has to pass the first filter medium 4 without bypass. The filter holder 6 has a second connector structure 9 for releasably and mechanically and sealingly attaching to a mating connector structure 10 of the intermediate connector 12 such that all fluid passing the first filter medium 4 is directed to the inlet 3*a* of the second filter funnel 3 via the intermediate connector 12.

The filter holder 6 can have a third connector structure 11 different from the second connector structure 9 for releasably and mechanically and sealingly attaching to a mating connector structure of a downstream equipment such that all fluid passing the first filter medium 4 is directed to the downstream equipment which could be the second filter funnel 3. The connector structures can be bayonet-type connector structures or threaded connector structures or snap-fit connector structures or force-fit connector structures or other mechanical connector structures that provide a sufficiently rigid connection and a fluid-tight connection. If necessary, sealing elements in the form of O-rings or other gaskets can be provided to establish fluid-tightness.

The intermediate connector 12 is connected to or is releasably connectable between the filter holder 6 and the inlet 3*a* of the second filter funnel 3. To this end, it has mating connector structures providing for a releasable and fluid-tight connection with the two elements, i.e. the connector structure 10 for the filter holder 6 and a further connector structure 18 for the inlet 3a of the second filter funnel 3. The intermediate connector 12 can be provided with one or two O-rings to ensure air integrity between the filter stages or funnels up- and downstream thereof (indicated with small circles in FIG. 1). The intermediate connector 12 can be in the form of a ring or adapter-like component as shown in the drawing. It can be a separate element or can be integral with the filter holder 6.

The intermediate connector 12 has a port 13, preferably at a lateral sidewall. The port is connectable to an external valve arrangement 14 via tubing. Alternatively, the valve arrangement, that can be in different alternatives as described below, can be integrated into the intermediate connector (not shown in the drawing).

The valve arrangement may comprise, in one alternative, a three-way valve 14a as shown in FIGS. 1 and 2 that can be switched between different positions to allow a selective communication of the internal space 3c of the second filter funnel 3 via the port 13 with an external gas source/atmosphere and/or a vacuum source. In an alternative structure, the valve arrangement 14 may comprise a calibrated leak 14b adapted to communicate the internal space 3c of the second filter funnel 3 via the port 13 of the intermediate connector 12 with the external gas source/atmosphere. This arrangement is shown in FIG. 3.

To connect the second or most downstream filter funnel with a downstream receptacle for receiving the filtrate or with downstream process equipment, it can be directly attached to such receptacle or equipment via the connector structure 7 or through a separate adapter-like structure that corresponds to the filter holder 6 in terms of the connector structures and the fact that it supports a membrane 5. In this case the filter holder can have a third connector structure 11 as well for connection to a downstream receptacle or other process equipment. Such filter holder 6 is provided with the second filter medium 5 which can serve as the main-filter medium or can represent a further pre-filter stage depending on the filtration requirements.

As shown in FIG. 1 a lid 15 can be provided so as to be releasably attachable to close the inlet 2a of the first filter funnel 2 (or of all the filter funnels if they are identical in dimension). The first filter funnel (or all the filter funnels) and the lid 15 can be made disposable, preferably from a plastics material. They can also be completely or partially transparent to allow visual inspection of the fluid level in the respective internal spaces. A partial transparency can be realized by a window-like transparent insert in an otherwise non-transparent material. Alternatively, the complete part can be made from a transparent material like glass or plastic.

The FIGS. 2a to 2e show a sequence of steps in a typical filtration process of filtering a complex fluid sample using the filter device of the present invention that is shown in FIG. 1. In this example, the first filter funnel 2 is a pre-filtration funnel A and the second filter funnel 3 is a main filtration funnel B. The filter device is placed on a filter head 16 and is further identified as D which communicates with a vacuum source. The three-way valve 14a is further identified as C and is connected with one of its ports to the port 13 of the intermediate connector 12, with another one of its ports to the filter head 16 via a tubing 17, and with the third of its ports with the normal atmosphere (or any other defined atmosphere or gas-source).

In the first step (FIG. 2a), a predefined desired volume of a complex to sample fluid is placed in the first filter funnel A and the three-way valve C is set such that a communication is provided between the internal space of the second filter funnel B with the vacuum source existing in the filter head D. The vacuum or sub-ambient pressure promotes filtration of the fluid sample through the first or pre-filter between the first and second filter funnels. In the second step (FIG. 2b) the filtration is still in progress and in the third step (FIG. 2c) all the fluid of the sample is received in the second filter funnel B. At this step, the three-way valve C is set to a position such that the vacuum source is disconnected from the internal space of the second filter funnel B and a communication is established between the atmosphere (or external gas source) with the internal space of the second filter funnel B. This promotes quick further filtration of the sample fluid through the second or main filter upstream the outlet of the second filter funnel B to the downstream equipment (or receptacle) D until, in the fourth step (FIG. 2d), all the fluid of the sample has been processed.

Figure 2A:
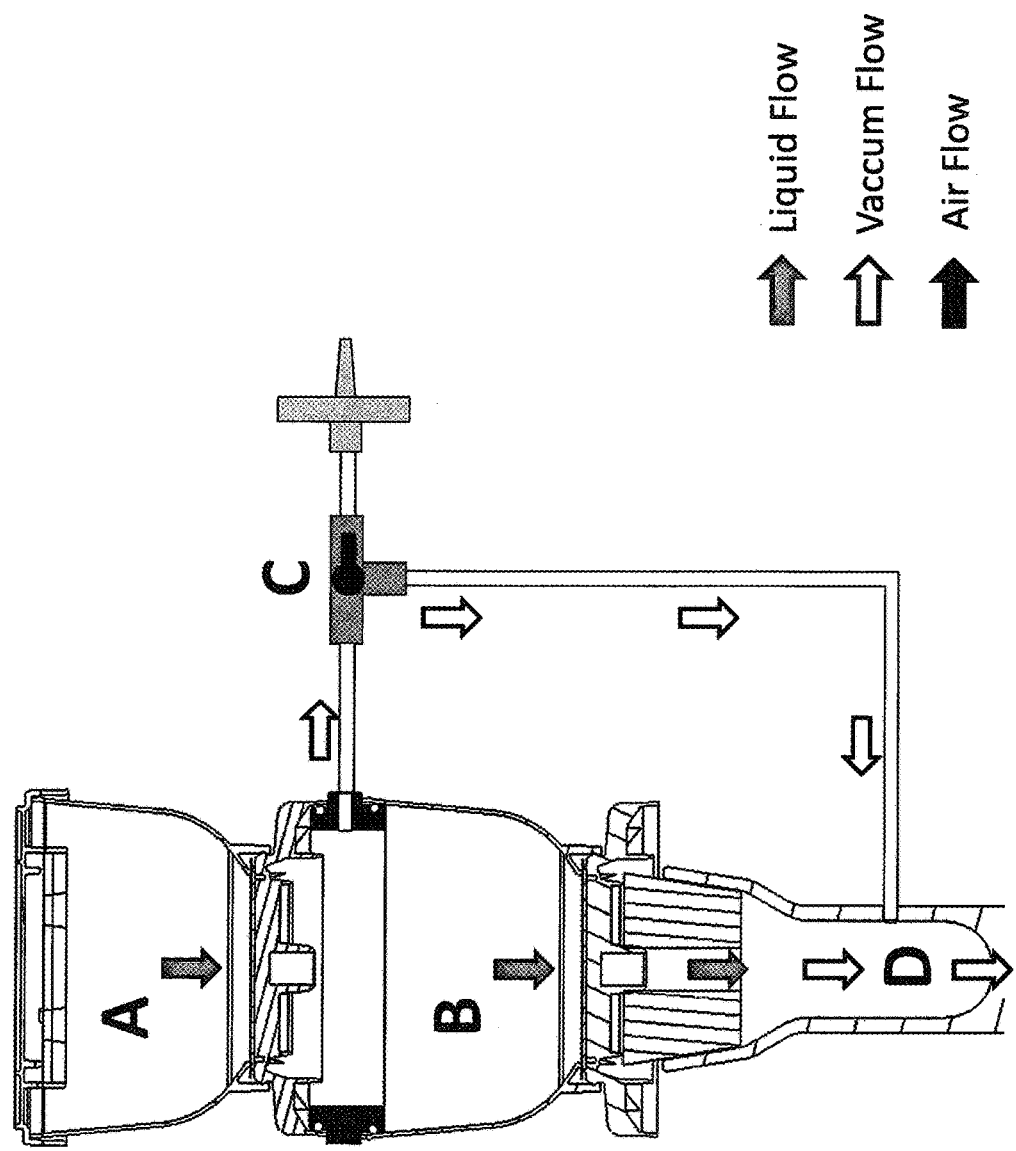
FIG. 2 shows a typical sequence of steps of filtering a complex fluid sample through the filter device of FIG. 1.
Figure 2B:
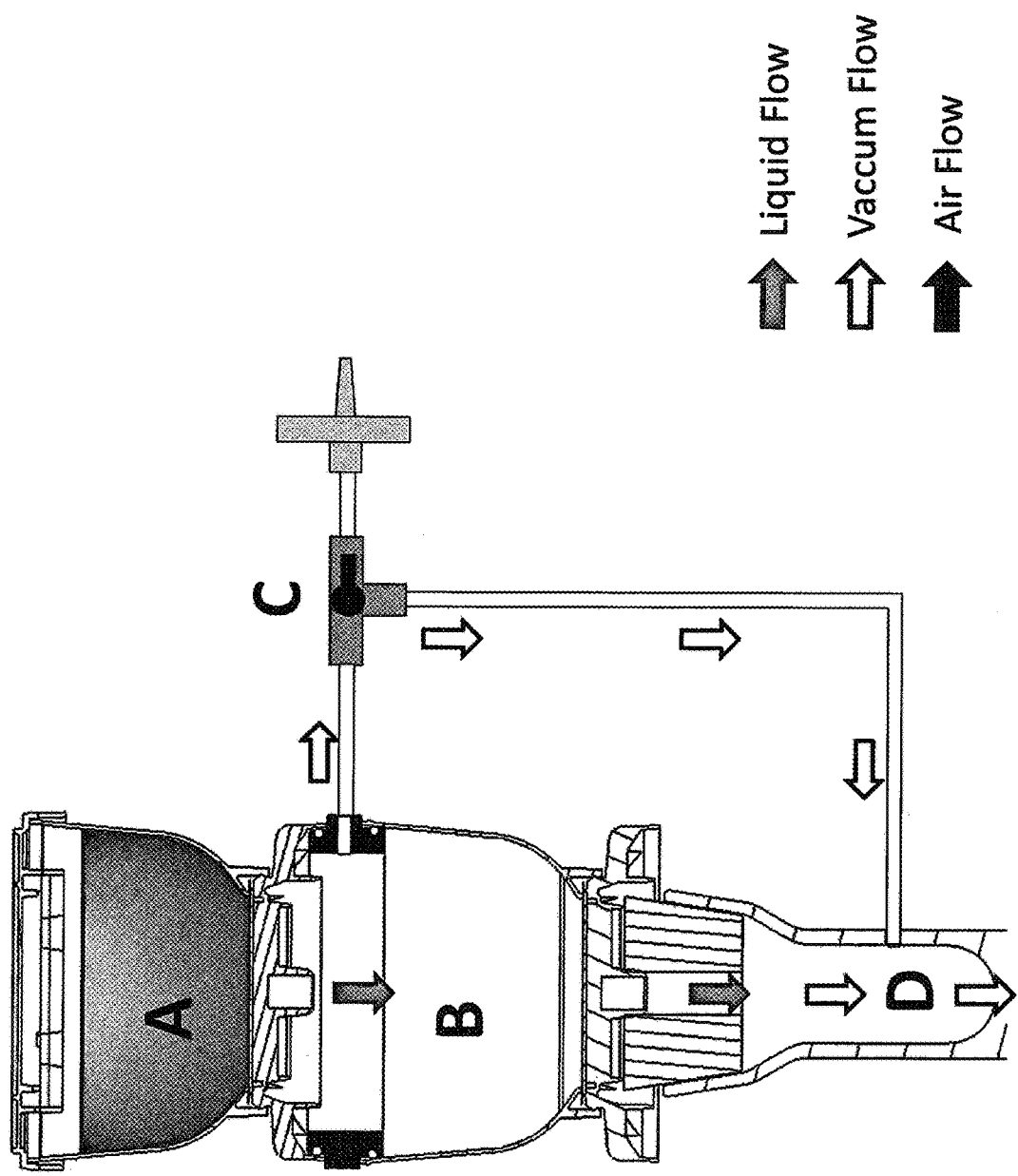
Figure 2C:
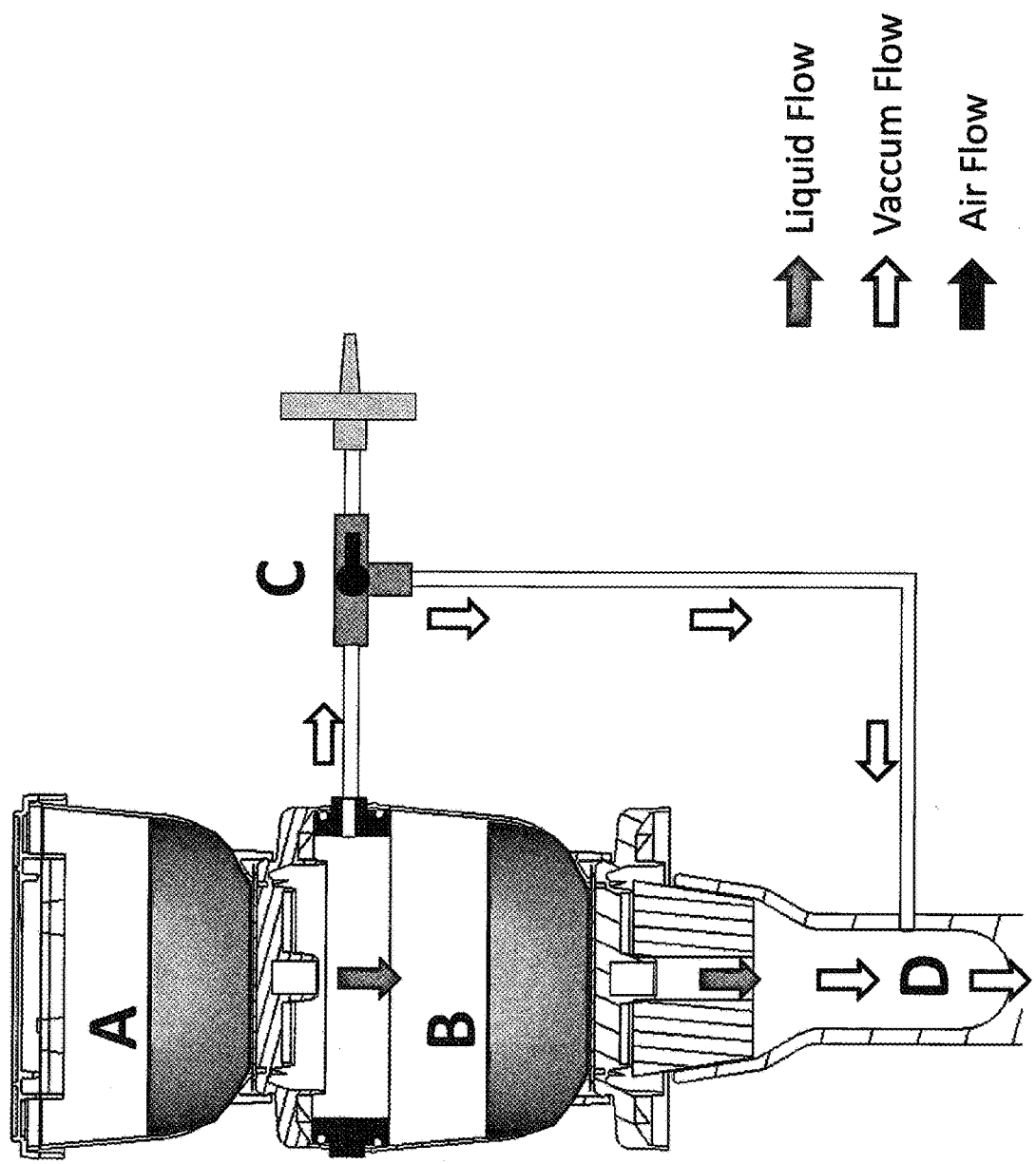
Figure 2E:
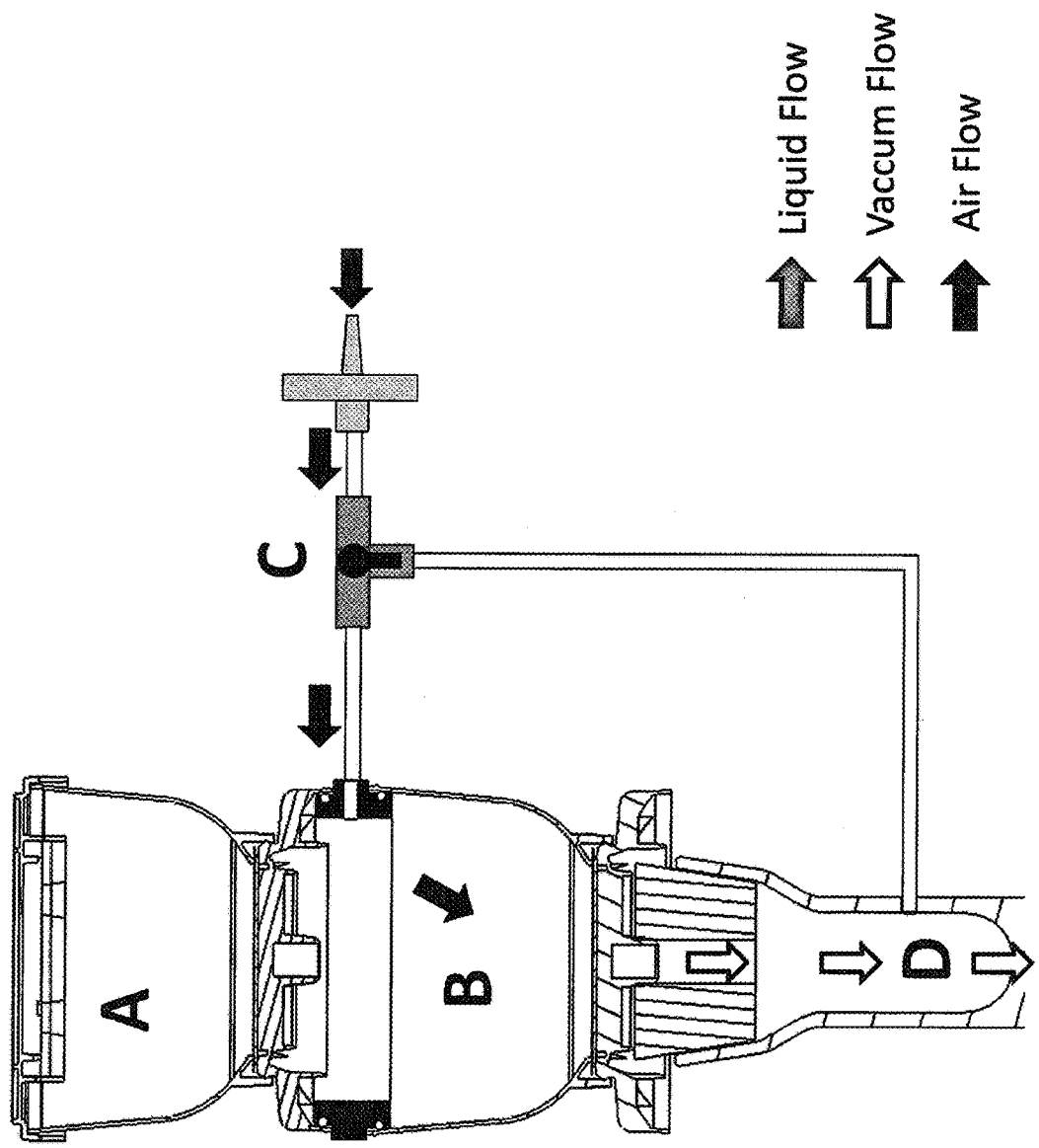
Figure 2F:
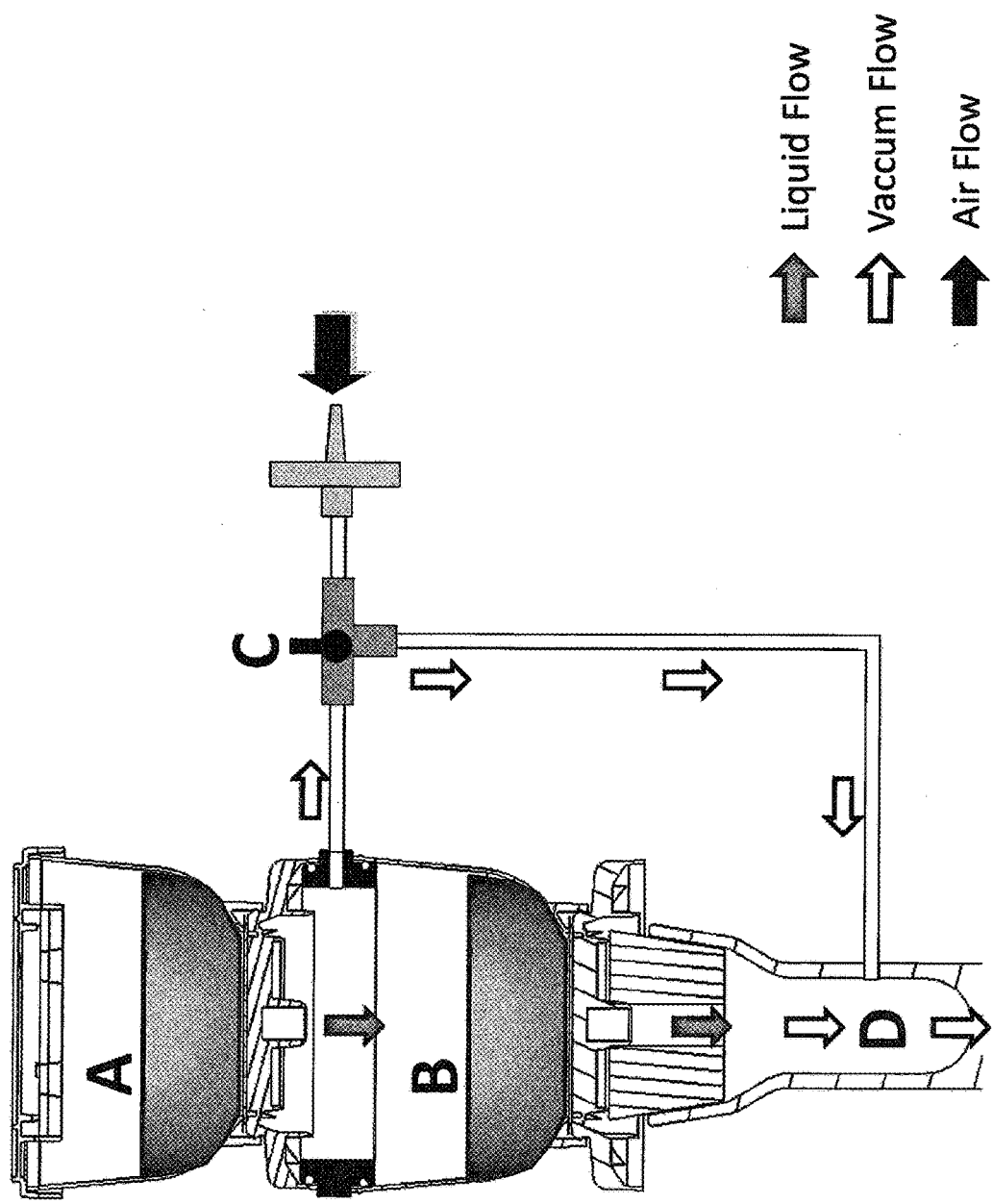
Figure 3A:
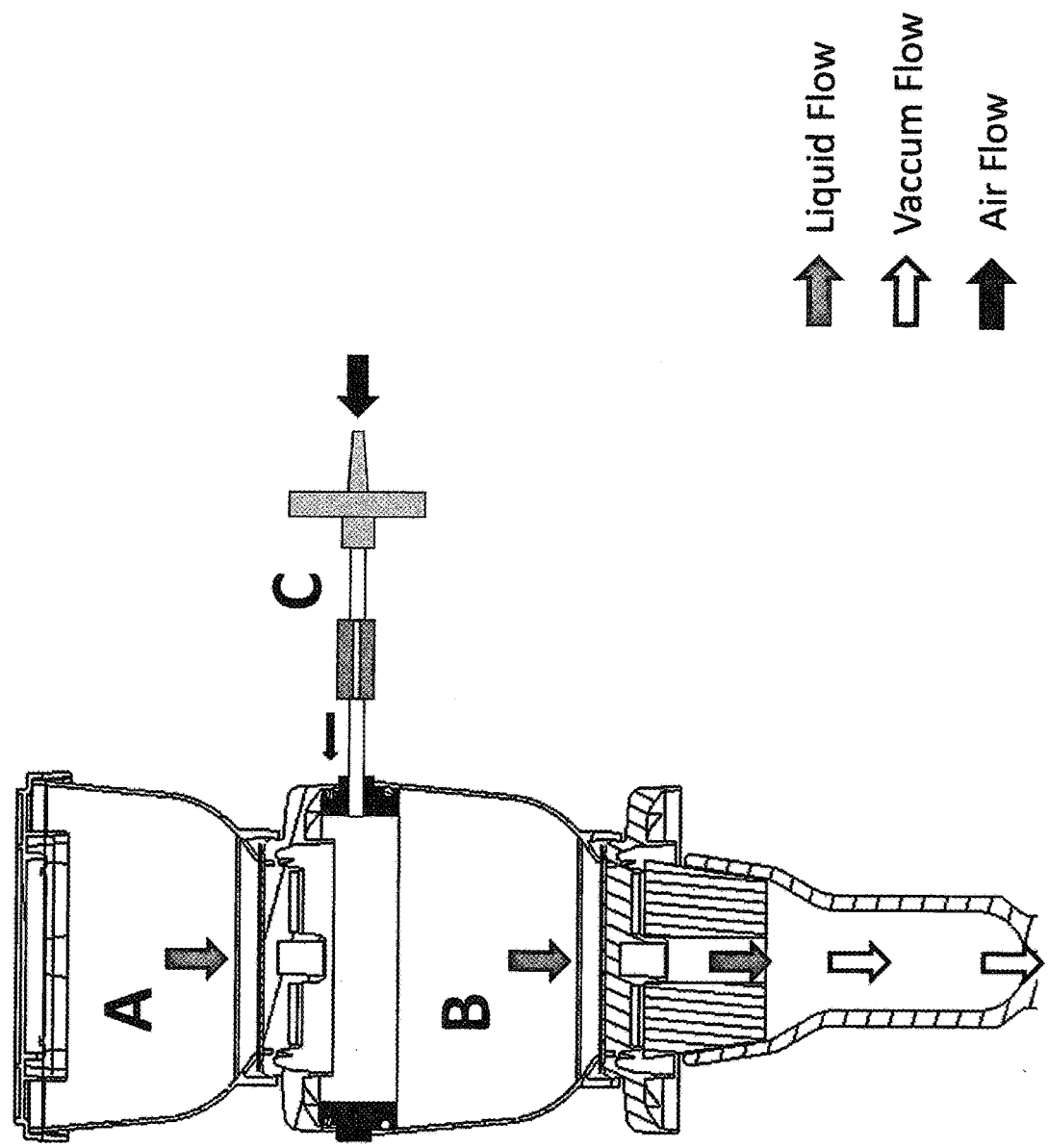
FIG. 3 shows a typical sequence of steps for filtering a complex fluid sample using a modified filter device that has a calibrated leak as a valve arrangement instead of the three-way valve employed in the device of FIG. 2.
Figure 3B:
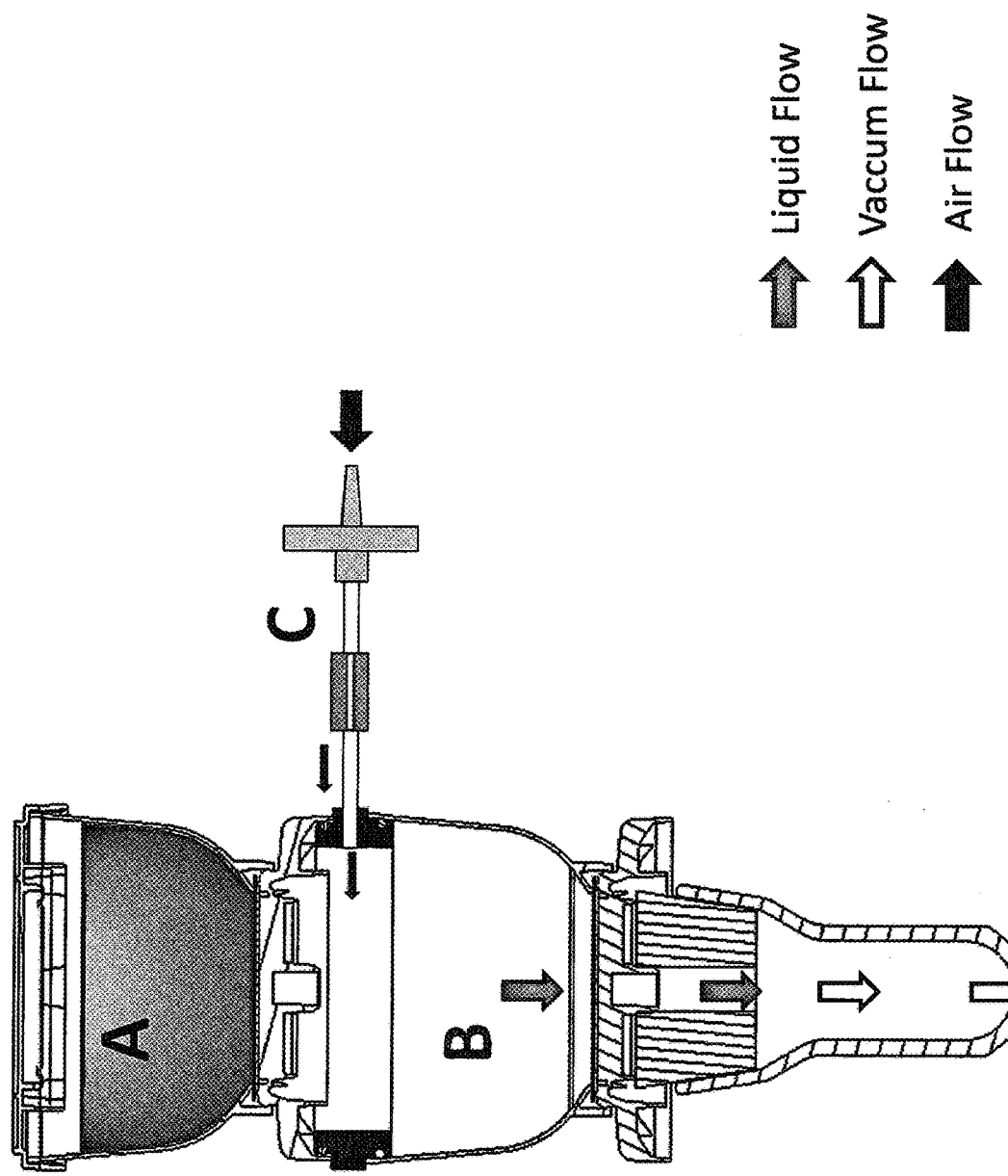
Figure 3D:
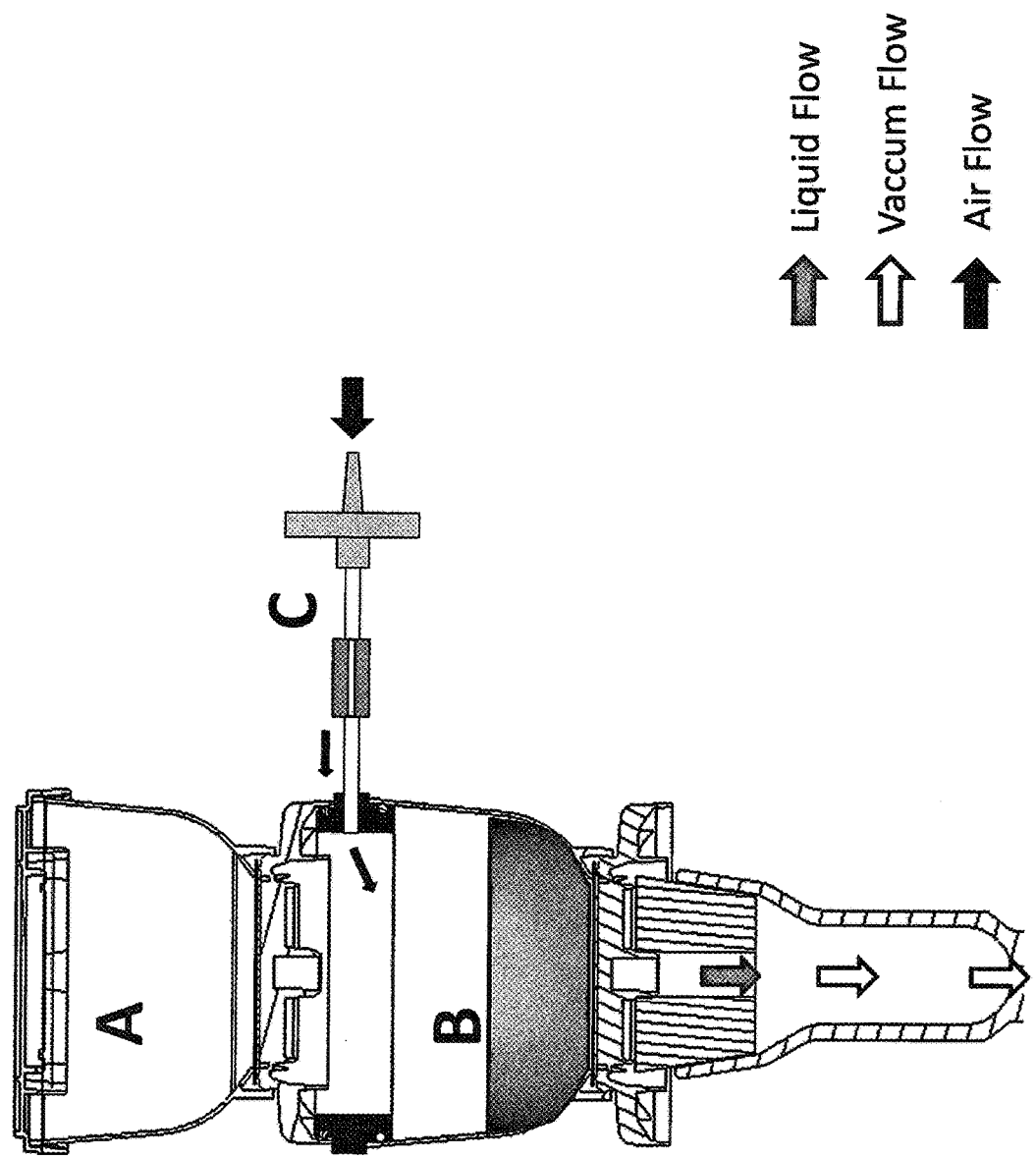

As shown in FIG. 2f, the control of a vacuum level applied on the filtration device A through the valve C during filtration from the first to the second filter funnel can require an opening to the atmosphere during filtration.

In an alternative example which is preferable for filtration tasks that do not require an additional vacuum or sub-ambient pressure for the pre-filtration, the three-way valve can be replaced by a calibrated leak 14b as shown in FIG. 3. The use of the calibrated leak with a connection to the atmosphere (i.e. a vent) can help avoiding foams and splashes in the filtered fluid in such a case and can assist avoiding deforming of the membrane on the filter holder(s).

The calibrated leak 14b can be replaced by a two-way valve that can be set between an open and a closed position and, if necessary, intermediate partially-opened positions, and/or a further vent (not shown) in the intermediate connector that is permanently open or can be selectively opened. Such a vent can allow a reduction of the vacuum level applied to the filtration device A and return to atmosphere in filtration device B. The calibrated leak can be realized in several ways, for example a hole of pre-defined size in the intermediate connector itself or in a separate element as shown in FIG. 3 connected to the port or, as described above, by a two-part valve or dedicated pressure reducer. The calibrated leak has to be adapted to the vacuum system used for filtration and has to be set or calibrated such that the amount of air passing the calibrated leak is always smaller than the level of vacuum applied to the second filter funnel. A similar effect can be obtained by the three-way valve 14a in that it is only partially opened. The calibrated leak is, however, advantageous in that it avoids any manipulation and is pre-set for a particular filtration arrangement and avoids any external connections.

According to the description above the vacuum source is existing in the downstream filter head. It can, however, be applied by an external separate dedicated vacuum source or pump and connected to the port 13 of the intermediate connector 12. The provision of an external dedicated vacuum source is preferable because it provides an autonomous two-stage filtration with the device of the invention.

The invention has been described on the basis of an embodiment where the first and second filter funnels and the connector are formed as separate components and assembled together, preferably in a releasable manner. However, the entire filter device, except the filter media, may also be embodied partly or entirely as an integral unit that is either formed from the same material or assembled together from separately manufactured components in a manner that they cannot be taken apart without destruction.

The invention claimed is:

1. A filter device (1) for filtering complex fluid samples, comprising:

a first filter funnel (2) having an inlet (2a), an outlet (2b) and an internal space (2c) dimensioned to receive a volume of sample fluid to be filtered, wherein said internal space (2c) is positioned between said inlet (2a) and said outlet (2b);

a second filter funnel (3) having an inlet (3a), an outlet (3b) and an internal space (3c) dimensioned to receive the volume of sample fluid, wherein said internal space (3c) is positioned between said inlet (3a) and said outlet (3b);

wherein said first and second filter funnels (2,3) are sequentially arranged with a first filter medium (4) located therebetween such that the volume of sample fluid placed in the internal space (2c) of the first filter funnel (2) can pass through the first filter medium (4) and be collected in the internal space (3c) of the second filter funnel (3);

an intermediate connector (12) provided between said first filter medium (4) and said internal space (3c) of the second filter funnel (3), said intermediate connector (12) having a port (13) and/or a vent; and a valve arrangement (14) connected to said port (13) and/or a vent for communicating said internal space (3c) of said second filter funnel (3) with an external gas source/atmosphere and/or a vacuum source via said valve arrangement (14), wherein said first filter medium (4) is a pre-filter and said second filter funnel (3) includes a second filter medium (5).

2. The filter device (1) according to claim 1, wherein the first and second filter funnels (2,3) are integrally connected with each other.

3. The filter device (1) according to claim 2, further comprising a filter holder (6) to support said first filter medium (4), wherein said first and second filter funnels (2,3) are connectable through said filter holder (6).

4. The filter device (1) according to claim 3, wherein said first filter funnel (2) includes a first connector structure (7) for releasably mechanically and sealingly attaching a mating connector structure (8) of said filter holder (6) to said first filter funnel (2) such that fluid placed in said internal space (2c) of said first filter funnel (2) can be discharged through said first filter medium (4).

5. The filter device (1) according to claim 4, wherein said filter holder (6) further comprises a second connector structure (9) for releasably mechanically and sealingly attaching said filter holder (6) to a mating connector structure (10) of said intermediate connector (12) such that all fluid passing through said first filter medium (4) is directed to said inlet (3a) of said second filter funnel (3).

6. The filter device (1) according to claim 5, wherein said filter holder (6) has a third connector structure (11), which is different from said second connector structure (9), for releasably mechanically and sealingly said filter holder (6) attaching to a mating connector structure of a downstream equipment.

7. The filter device (1) according to claim 3, wherein said intermediate connector (12) is connected between said filter holder (6) and said inlet (3a) of said second filter funnel (3).

8. The filter device (1) according to claim 1, wherein said valve arrangement (14) comprises a 2-way valve or a 3-way valve (14a) and tubing adapted to selectively communicate said internal space (3c) of said second filter funnel (3) via said port (13) and/or vent of the intermediate connector (12) with an external gas source/atmosphere and/or vacuum source.

9. The filter device (1) according to claim 1, wherein said valve arrangement (14) comprises means for (14b) providing communication between said internal space (3c) of said second filter funnel (3) via said port (13) and/or vent of said intermediate connector (12) with an external gas source/atmosphere.

10. The filter device (1) according to claim 1, wherein said valve arrangement (14) is integral with said intermediate connector (12) or is externally connected or is externally connectable to said port (13) and/or vent of said intermediate connector (12).

11. The filter device (1) according to claim 1, wherein said first and/or second filter funnels (2,3) is/are at least partially transparent to allow visual inspection of fluid level in the internal space (2c,3c) of the first filter funnel and/or of the second filter funnel.

12. The filter device (1) according to claim 1, further comprising a lid (15) releasably attachable to close said inlet (2a) of said first filter funnel (2).

13. The filter device (1) according to claim 1, wherein said first filter funnel (2) is made from a plastic material.

14. The filter device (1) according to claim 1, wherein said first and second filter funnels (2,3) are identical in structure.

15. A combination of a filter device (1) according to claim 1 and a vacuum source connected to said filter device via said valve arrangement (14).

16. The filter device (1) according to claim 1, wherein the first and second filter funnels (2,3) are releasably connectable with each other.

17. The filter device (1) according to claim 3, wherein said intermediate connector (12) is releasably connectable between said filter holder (6) and said inlet (3a) of said second filter funnel (3).

18. The filter device (1) according to claim 10, wherein said valve arrangement (14) is a 2- or 3-way valve (14a).

19. The filter device (1) according to claim 10, wherein said valve arrangement (14) comprises means for (14b) providing communication between said internal space (3c) of said second filter funnel (3) via said port (13) and/or vent of said intermediate connector (12) with an external gas source/atmosphere.

20. A filter device (1) for filtering complex fluid samples, comprising:

a first filter funnel (2) having an inlet (2a), an outlet (2b) and an internal space (2c) dimensioned to receive a volume of sample fluid to be filtered, wherein said internal space (2c) is positioned between said inlet (2a) and said outlet (2b);

a second filter funnel (3) having an inlet (3a), an outlet (3b) and an internal space (3c) dimensioned to receive the volume of sample fluid, wherein said internal space (3c) is positioned between said inlet (3a) and said outlet (3b);

wherein said first and second filter funnels (2,3) are sequentially arranged with a first filter medium (4) located therebetween such that the volume of sample fluid placed in the internal space (2c) of the first filter funnel (2) can pass through the first filter medium (4) and be collected in the internal space (3c) of the second filter funnel (3); and an intermediate connector (12) provided between said first filter medium (4) and said internal space (3c) of the second filter funnel (3), said intermediate connector (12) having a port (13) and/or a vent for communicating said internal space (3c) of said second filter funnel (3) with an external gas source/atmosphere and/or a vacuum source, wherein said first filter medium (4) is a pre-filter and said second filter funnel (3) includes a second filter medium (5).

\* \* \* \* \*